United States Patent [19]

Donn et al.

[11] Patent Number: 5,074,875
[45] Date of Patent: * Dec. 24, 1991

[54] INTRAOCULAR-EXTERNAL LENS COMBINATION SYSTEM AND METHOD OF USING SAME

[76] Inventors: Anthony Donn, 635 W. 165th St., New York, N.Y. 10032; Charles J. Koester, 60 Kent Rd., Glen Rock, N.J. 07452

[*] Notice: The portion of the term of this patent subsequent to Dec. 8, 2004 has been disclaimed.

[21] Appl. No.: 432,852

[22] Filed: Nov. 7, 1989

Related U.S. Application Data

[63] Continuation of Ser. No. 289,459, Dec. 22, 1988, abandoned, which is a continuation of Ser. No. 218,820, Jul. 12, 1988, abandoned, which is a continuation of Ser. No. 109,165, Oct. 16, 1987, abandoned, which is a continuation of Ser. No. 316,920, Oct. 30, 1981, Pat. No. 4,710,197.

[51] Int. Cl.$^5$ .............................................. A61F 2/16
[52] U.S. Cl. ................................... 623/6; 351/160 R
[58] Field of Search ................ 623/6; 351/159, 160 R

[56] References Cited

U.S. PATENT DOCUMENTS

| | | |
|---|---|---|
| 2,078,590 | 4/1937 | Spero . |
| 2,164,801 | 7/1939 | Dittmer ........................... 351/160 R |
| 2,834,023 | 5/1958 | Lieb ..................................... 623/6 R |
| 3,027,803 | 4/1962 | Filderman . |
| 4,010,496 | 3/1977 | Neefe ..................................... 623/6 |
| 4,041,552 | 8/1977 | Ganias ..................................... 623/6 |
| 4,074,368 | 2/1978 | Levy, Jr. et al. ......................... 623/6 |
| 4,092,743 | 6/1978 | Kelman ..................................... 623/6 |
| 4,159,546 | 7/1979 | Shearing ..................................... 623/6 |
| 4,244,060 | 1/1981 | Hoffer ..................................... 623/6 |
| 4,251,887 | 2/1981 | Anis ..................................... 623/6 |
| 4,435,855 | 3/1984 | Pannu ..................................... 623/6 |
| 4,710,197 | 12/1987 | Donn et al. ............................. 623/6 |

FOREIGN PATENT DOCUMENTS 1103399 5/1955 France ................................... 623/6

OTHER PUBLICATIONS

"Experience with Twelve Cases of Intra-Ocular Anterior Chamber Implants for Aphakia" by J. Boberg Ans. British Journal of Ophthalmology, vol. 45, No. 1, Jan. 1961, pp. 37–43.
Choyce, "Intra-Ocular Lenses and Implants" (1964), Chapters 1 and 2.
Choyce, "History of Intraocular Implants" (1973), pp. 1113–1120.
Binkhorst, "The Optical Design of Intraocular Lens Implants" (1975), pp. 17–30.
Article by Troutman—"Artiphakia and Aniseikonia", —American Journal of Ophthalmology, pp. 602–639, Oct. 1963.
Article by ISEN—"Feinbloom Mini—Scope Contact Lens"—Encyclopedia of Contact Lens Practice, Nov. 15, 1961.
Choyce, Peter A. 1964, "Intra-Ocular Lenses and Implants", H. K. Lewis & Co., Ltd., London, pp. 156–161.

Primary Examiner—Ronald Frinks
Attorney, Agent, or Firm—Sandler, Greenblum & Bernstein

[57] ABSTRACT

An intraocular lens system including a lens having a negative-powered section for use in combination with a positive-powered external lens system. The intraocular lens is preferably positioned in the posterior chamber of the eye and is configured so as to provide maximum separation between the intraocular lens and the external lens system, thereby achieving maximum magnification and field of view. Alternatively, the refracting powers of the lens system can be reversed, thus resulting in image demagnification.

25 Claims, 7 Drawing Sheets

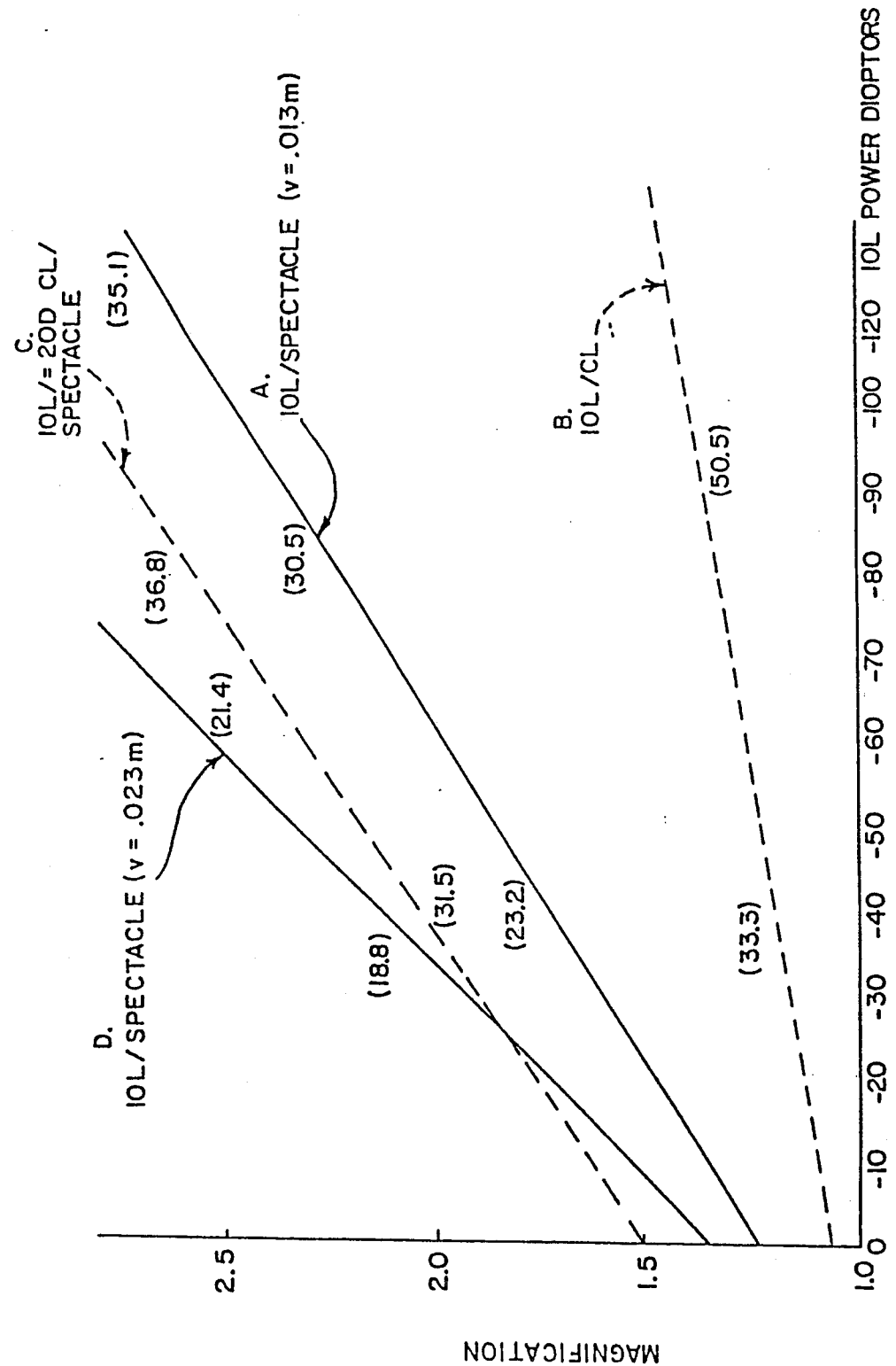

INTRAOCULAR-EXTERNAL LENS COMBINATION SYSTEM AND METHOD OF USING SAME

This is a continuation of application Ser. No. 289,459, filed Dec. 22, 1988, now abandoned, which is a continuation of U.S. Ser. No. 218,820, filed July 12, 1988, now abandoned, which is a continuation of U.S. Ser. No. 109,165, filed Oct. 16, 1987, now abandoned, which is in in turn a continuation of U.S. Ser. No. 316,920, filed Oct. 30, 1981, now U.S. Pat. No. 4,710,197, issued Dec. 10, 1987.

BACKGROUND OF THE INVENTION

1. Field of the Invention

The invention relates to an intraocular lens for use in combination with an external lens system to form an image on the retina.

2. General State of the Art

One of the leading causes of blindness in America is macular degeneration. In this condition, the central retina, which perceives fine detail, is deficient. In the less severe cases of this disease, patients can often be helped by simple magnifiers or by various telescopes, both of which serve to enlarge the image formed on the retina.

Magnifiers are used for reading or other tasks involving near vision. A variety of magnifiers are available and are generally useful for their intended purpose. However, such magnifiers are bulky and inconvenient and are of no help in other tasks such as walking about. Such magnifiers are likewise tiring to the user, thus detracting from their usefulness.

For improved distant vision, a telescope is required. In order to be suitable for low vision patients, telescopes must be compact, light weight, and reasonably inexpensive. These requirements together with basic optical limitations generally result in a device which magnifies but with an enormous loss of visual field. For the low vision patient, with his natural lens, telescopes of 2.2×, 2.5×, or 3× are often prescribed for use outdoors, or for other distance viewing. The field loss is so great that most patients with macular degeneration do not find telescopes of much practical value. Such telescopes are, therefore, often of limited practical use because of their narrow field, poor cosmetic appearance and difficulty in fitting to the patients face. As a result, they are used relatively infrequently by patients.

When patients have cataracts in addition to macular degeneration, the prognosis is even worse. Removal of the cataract, followed by vision correction with spectacles or contact lenses, renders the field of vision smaller without significantly improving magnification.

The aphakic patient with a normal retina faces a formidable optical problem. Spectacle lenses of +11 to +16 diopters are needed to provide the required additional focusing power. The lenses are thick and must be precisely fitted to the patient's face. Furthermore, the field of view is restricted by the size and the refracting effect of the lenses. Alternatively, contact lenses of similar power may be worn. However, a substantial number of patients, particularly older patients with limited finger dexterity, cannot wear contact lenses.

If the aphakic patient further has macular degeneration, the conventional telescopic low-vision aids mounted on the spectacle frame will be a problem. The telescope adds weight, and projects beyond the already large spectacle lenses. The telescope further limits the field of vision. The field problem is aggravated by the fact that the presence of the spectacle lens moves the telescope yet further from the eye than the optimum position.

Some aphakic low-vision patients can use a 6× or 8× hand-held telescope. The 6× has a field of view of 11°, while the 8× has a field of 8°. Yet, this solution is not viable for the many patients who do not have the steadiness of hand to use such hand-held telescopes.

As a result of the above optical problems and the already reduced visual acuity, low-vision patients who develop cataracts are often not operated on.

Conversely, in other instances demagnification of the optical image is desirable. Thus, patients with retinitus pigmentosa (RP) and some patients with advanced glaucoma suffer a loss of peripheral vision. In order to function normally, e.g., to cross the street, they may benefit from a visual aid that demagnifies the retinal image, thus putting more of the visual field onto the central portion of the retina that is still functional.

The principle of the invention and the various embodiments disclosed herein overcome the above deficiencies while achieving the objectives set forth.

A search of the prior art has uncovered the following materials:

TROUTMAN, in an article entitled "Artiphakia and Aniseikonia", which appeared in the *American Journal of Ophthalmology*, pages 602–639, October, 1963, discusses the state of the art in artificial intraocular lenses. On page 614, the article states: "There is no reference in the literature on intra-ocular lenses as to the telescopic magnification which can be attained with the combination of an intraocular lens and a spectacle lens."

LEVY, Jr. et al., U.S. Pat. No. 4,074,368, disclose an intraocular lens that is based on the principle of a Galilean telescope wherein both the negative element 18 and the positive element 14 are fastened together, and both placed within the eye. Positive element 14 is an air lens formed by bubble 15, and negative element 18 is an air lens formed by bubbles 20 and 22. The patent suggests implantation of this intraocular lens system for relief of conditions such as macular degeneration and diabetic retinopathy.

LIEB, U.S. Pat. No. 2,834,023, discloses anterior chamber lenses for refractive correction of aphakia, high ametropia, and anisometropia, and bilateral and unilateral cataracts. Of particular interest are FIGS. 6–9, wherein lens 20 is of the diverging type.

FILDERMAN, U.S. Pat. No. 3,027,803, discloses a spectacle lens-contact lens system which forms a modified Galilean telescope. Contact lens 10 serves as the negative lens in the telescope lens system, and central segment L2 of spectacle lens L1 serves as the positive objective lens of the telescopic lens system. Furthermore, the patent discloses how a 2× magnification system can be developed by using a negative lens of −50 diopters and a positive lens of +25 diopters.

DITTMER, U.S. Pat. No. 2,164,801, discloses a corrective lens system wherein an alternate embodiment provides a telescopic lens system, as illustrated in FIG. 5. The telescopic lens system comprises negative contact lens 23 which is worn on eye 10, and positive spectacle lens 24 which is mounted in front of eye 10.

SPERO, U.S. Pat. No. 2,078,590, discloses telescopic spectacles wherein positive lens 15 is secured to glass carrier member 16, and negative lens 17 is secured to second glass member 18. The total lens system is secured to a spectacle lens mounting system.

ISEN, in "Feinbloom Mini-Scope Contact Lens" as reported in the *Encyclopedia of Contact Lens Practice* (Nov. 15, 1961), teaches making a Galilean lens system out of a doublet constructed contact lens. As can be seen, the negative lens is placed closest to the eye, while the positive objective lens is placed a small distance away from the eye.

SUMMARY OF THE INVENTION

It is an object of the invention to overcome the above disadvantages associated with conventional devices and techniques, and to provide a system allowing for improved vision with a greater field of vision than was previously possible.

It is a further object of the invention to provide an optical system which is useful for improving distant vision by patients having macular degeneration and aphakic patients and which is more acceptable cosmetically than are the presently available telescopic spectacles.

It is yet a further object of the invention to provide a system providing a demagnified retinal image thereby placing more of the visual field onto the central portion of the retina thus aiding patients suffering from loss of peripheral vision.

According to one embodiment of the invention, a negative-power intraocular lens is provided which is adapted to be positioned in the posterior chamber of the eye. The intraocular lens is configured so as to provide an enlarged retinal image and a large field of vision when used in combination with an exterior positive lens.

According to one preferred embodiment of the invention, the exterior lens is a spectacle lens, while in another embodiment the external lens is a positive contact lens.

A second external lens may also be provided. In this instance, the first external lens is a positive spectacle lens and the second external lens is a negative or a positive contact lens.

According to the invention, a method for providing improved magnification to human eyes having no natural lens is disclosed. The method comprises implanting a negative intraocular lens within the eye; and providing an external positive lens. A second external lens may be used, in which case the first external lens is a positive spectacle lens, and the second external lens is a negative or a positive contact lens.

According to a second aspect of the invention, the intraocular lens has a positive power while the external lens has a negative power. Such a combination provides a system which demagnifies the image to the retina while providing an improved field of vision. Once again, the external lens can be a lens system comprising two lenses; i.e., a spectacle and contact lens.

In the corresponding method, a positive IOL is implanted in an eye and is combined with an external negative lens so as to provide a demagnified image on the retina with an increased field of vision.

BRIEF DESCRIPTION OF THE DRAWINGS

FIG. 5 is a graph used for selecting the correct intraocular lens, depending upon the magnification desired;

DESCRIPTION OF PREFERRED EMBODIMENTS

Figure 1:
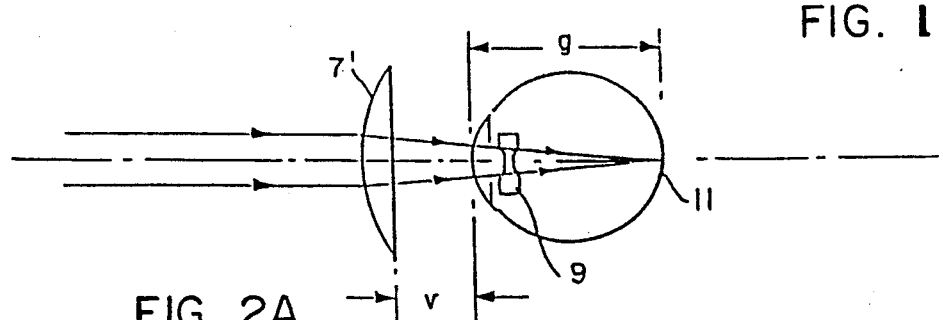
FIG. 1 is a cross-sectional view of one embodiment of an optical system of the invention.
Figure 7:
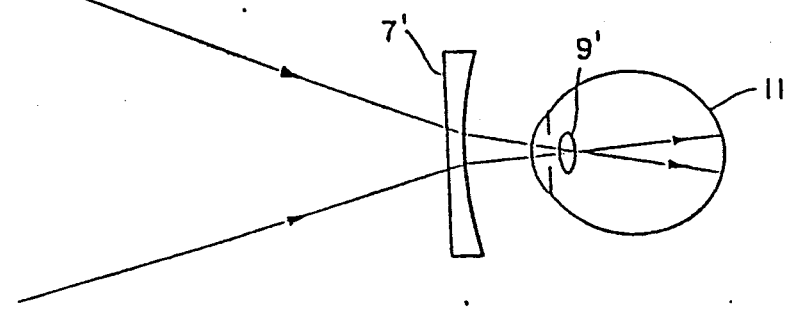
FIG. 7 is an alternative embodiment to the embodiment shown in FIG. 1 for demagnifying the visual image.

As was noted above, most broadly, the optical system of the invention includes an intraocular lens, such as is illustrated in FIGS. 1 and 2 (or FIG. 7). Referring to FIG. 1, the negative power of the intraocular lens is selected such that, when a spectacle lens or contact lens of appropriate power is worn, the patient will have a magnified retinal image.

As was noted previously, the intraocular lens may be used in combination with either a contact lens and/or a spectacle lens. When combined with a spectacle or contact lens of a positive power, the combination will behave as a Galilean telescope with a magnification factor greater than unity.

Figure 12:
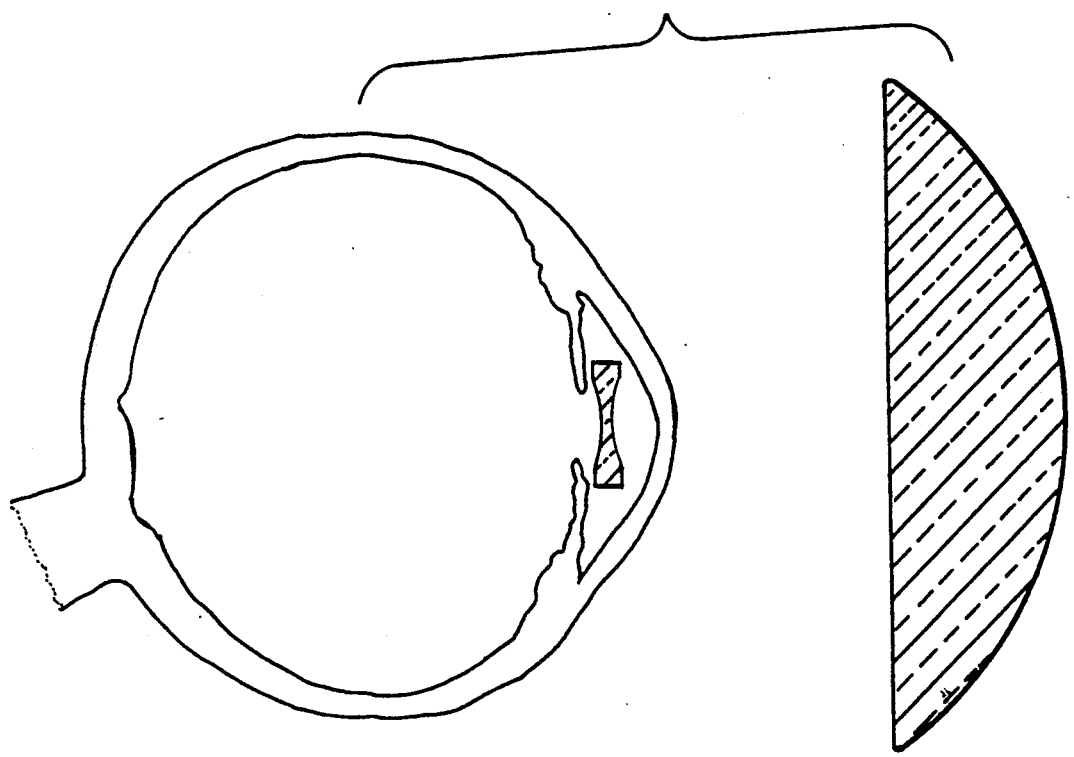
FIG. 12 illustrates a negative intraocular lens positioned in the anterior chamber in combination with a positive external spectacle lens.

As seen from FIG. 1, a spectacle lens 7 having a positive refracting power is worn in combination with the negative intraocular lens 9 so as to focus the image on the retina 11. The intraocular lens is positioned behind the iris. It is also possible, although far less preferable, to position the lens in the anterior portion of the eye, between the cornea and the iris (FIG. 12).

It is an advantage of the invention that the intraocular lens is positioned close to the pupil of the eye, thereby permitting the lens to be of relatively small size, as compared, for example, with negative-power contact or spectacle lenses which might otherwise be used for the same purpose. Additionally, by positioning the lens in the posterior chamber, maximum separation is achieved between the spectacle or contact lens used and the intraocular lens, thereby achieving maximum magnification.

The distance, v, shown in FIG. 1 is the vertex distance, defined as the separation between the vertex of the cornea and the vertex of the spectacle lens. As will be explained below, this distance is important in determining the magnification that is achieved.

The general intraocular lens structure contemplated is of the type which is generally known, such as, for example, the type disclosed in U.S. Pat. No. 4,041,552 to GANIAS, the disclosure of which is hereby incorporated by reference.

Figure 2A:
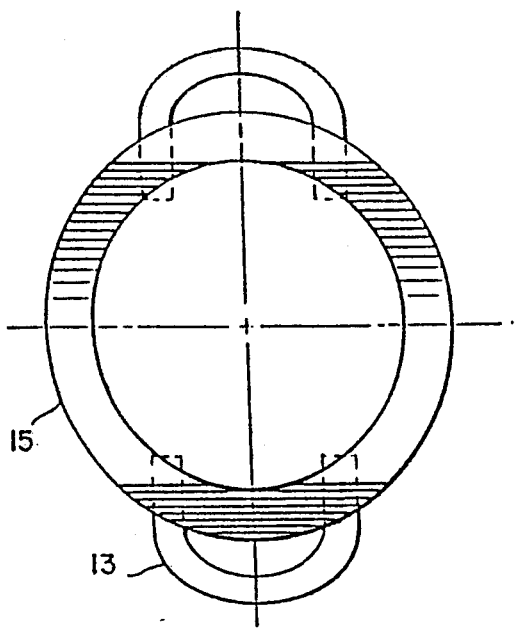
FIGS. 2A and 2B are front and side magnified cross-sectional views of the negative intraocular lens shown in FIG. 1.
Figure 2B:
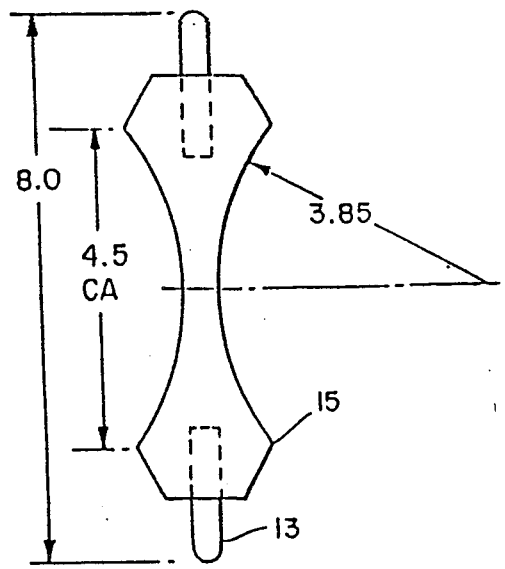

As may be seen from FIGS. 2A and 2B, the intraocular lens is provided with loops or haptics 13 of plastic or metal for holding the lens element 15 firmly in position. FIG. 2B illustrates relative dimensions in millimeters. The clear aperture (CA) in this example is 4.5 mm.

Figure 3A:
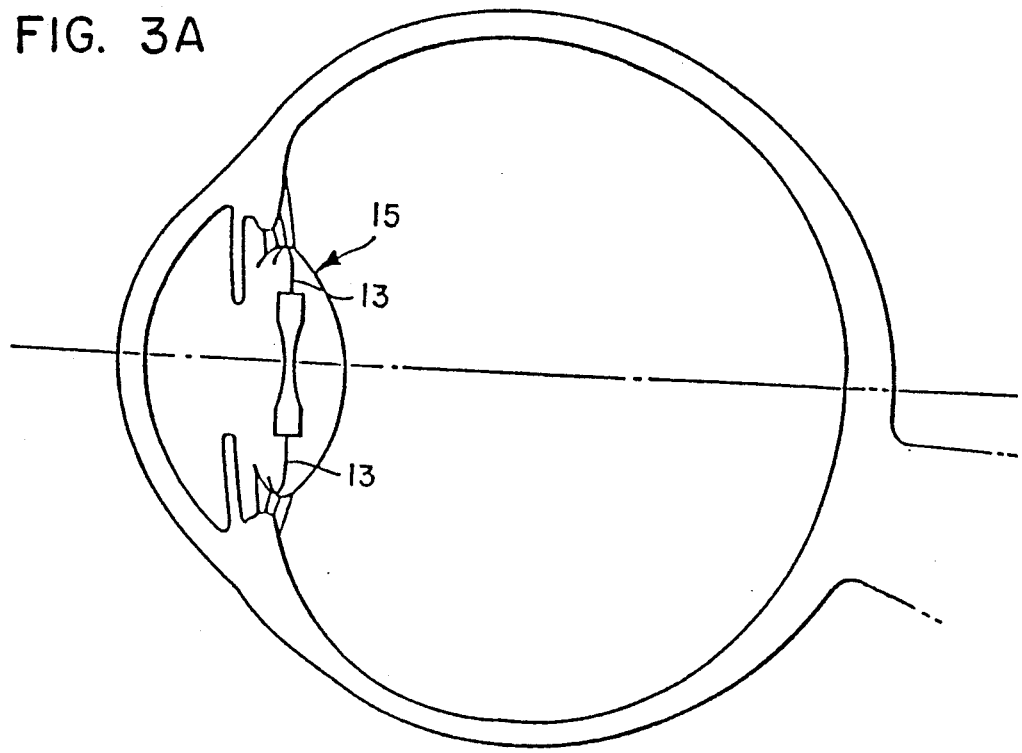
FIGS. 3A and 3B illustrate cross-sectional views of the intraocular lens inserted in the posterior chamber.
Figure 3B:
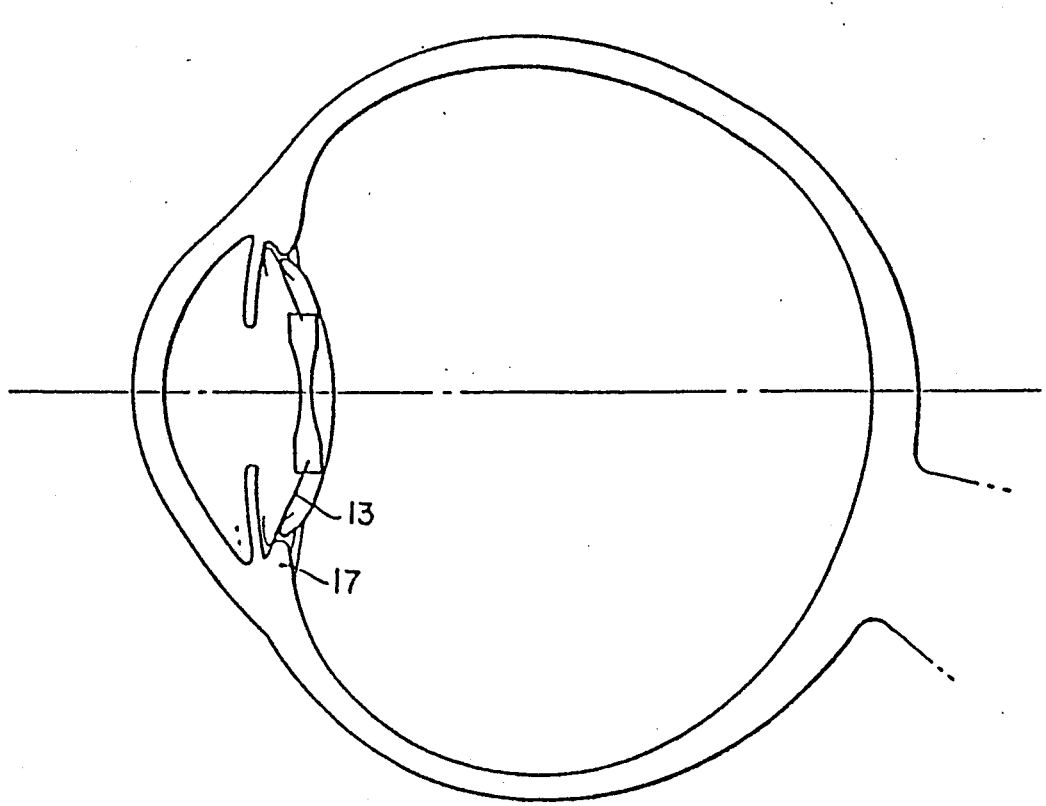

FIG. 3A shows one possible technique for positioning the lens in the posterior chamber of the eye. As illustrated, the haptics 13 expand by spring tension, contacting the inside surface of the capsule 15. In FIG. 3B, the situation is illustrated in which the capsule has been removed, as in an intracapsular extraction. In this case the loops 13 expand against the ciliary body 17 and thereby position the IOL. The loops are shown as being inclined with respect to the plane of the IOL, the purpose being to position the IOL in a posterior position thus providing added separation between the IOL and the exterior lens. The decision as to the type of IOL to use may be made at the time of surgery.

Naturally, in this embodiment, the intraocular lens and the spectacle and/or contact lens must be appropriately selected so as to provide the desired degree of magnification, and a sharply focused retinal image, while providing optimal field of vision.

The power, P, of the IOL can be calculated from the equation:

$$P = \frac{n}{g-b} \cdot \frac{nv + g(1 - vC) - FM}{nv + b(1 - vC)} \quad 1.$$

where
n = index of refraction of the intraocular media = 1.336
g = distance from cornea vertex to the retina (FIG. 1) in meters (m).
b = distance from cornea vertex to the IOL (m)
v = vertex distance of spectacle lens (m)
c = power of cornea, in diopters
F = focal length of normal (phakic) eye
M = magnification desired Once the power of the IOL has been determined from Equation 1, the power, S, of the spectacle lens can be found as follows:

$$S = -\frac{P(g-b)(n-bC) - n(n-gC)}{P(g-b)(vbC - b - nv) + n(nv + g - vgC)}$$

S is the power required for distant vision. If correction is needed for near vision, appropriate additional power can be added to S.

Figure 6:
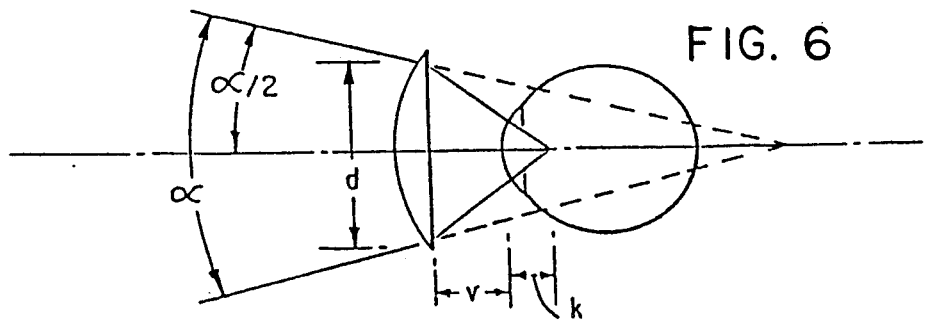
FIG. 6 is a diagram illustrating the field of view obtained through a spectacle lens.

The field of view is defined with the help of FIG. 6. The total angular field is defined as the angle $\alpha$.

$$\tan \frac{\alpha}{2} = \frac{d}{2}\left(\frac{1}{v+k} - S\right)$$

where
d = diameter of spectacle lens (m)
v = vertex distance from spectacle lens to the cornea (m)
k = distance from cornea vertex to nodal point of the eye (m). For the normal eye k = 0.007 m.
S = power of spectacle lens, in diopters.

Practically speaking, the procedure for selection of the appropriate lenses may be as follows. The patient's requirements for magnification and field of view are determined from a detailed examination, including visual acuity, if possible, and from determination of the patient's visual needs, e.g., distance vision vs. reading. From the available negative IOLs, the power that best meets the patient's requirments is selected. A graph such as that illustrated in FIG. 4 may be used for this purpose. The intraocular lens will have a power of −10 to −100 diopters with lenses of −40 diopters to −100 diopters being very suitable. After the implant surgery, when the eye has stabilized sufficiently, the patient is refracted to determine the best spectacle (or contact lens) for optimum vision.

Figure 9:
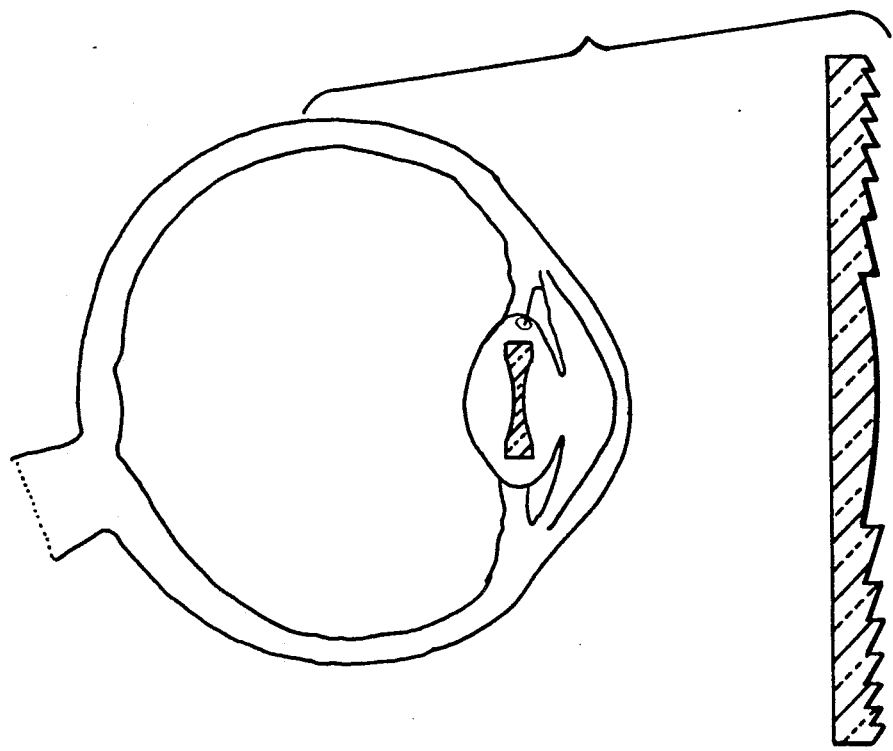
FIG. 9 illustrates a negative intraocular lens positioned in the posterior chamber in combination with an external fresnel lens.

The spectacle lens can be of the conventional glass or plastic type. It is also possible to use a positive Fresnel lens in some cases (FIG. 9), in order to reduce the weight of the spectacle. These lenses consist of thin plastic on which circular sections of a lens have been embossed. The finished piece acts as a lens, but the total thickness is much less than the conventional lens. They are especially useful in situations requiring large positive (or negative) dioptic powers.

Figure 4:
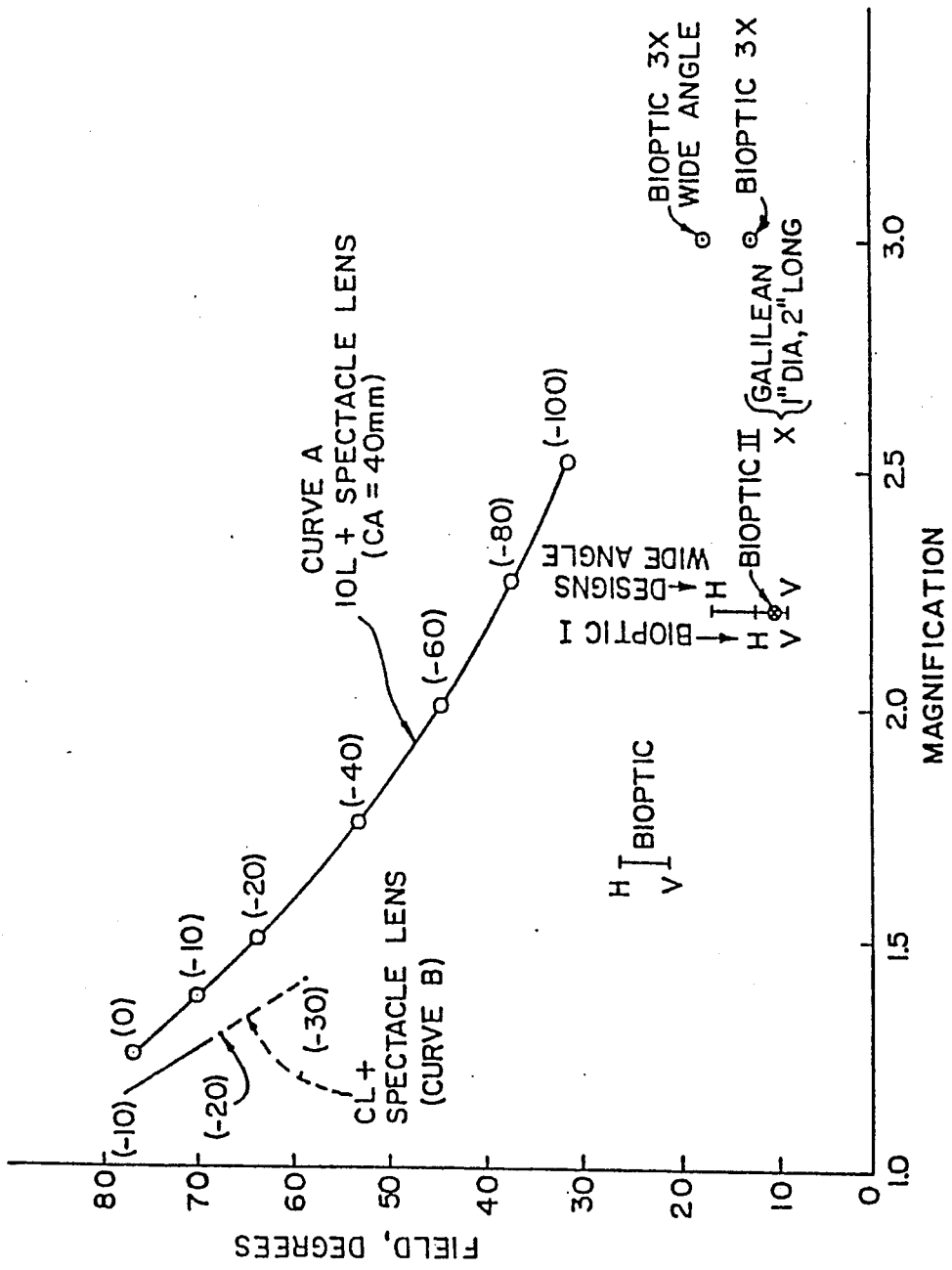
FIG. 4 is a graph comparing the magnification and field of vision of various optical systems, including the system of the invention.

FIG. 4 illustrates the magnification and field of view obtainable for the various IOL powers indicated in parentheses. For purposes of illustration, a fixed diameter of spectacle lens, 40 mm, was assumed. If a smaller diameter spectacle lens, or a spectacle lens that is not round is used, the field will be different from that shown. Also illustrated in FIG. 4 are the magnification and field obtainable in a number of currently available telescopic low vision aids, such as the Bioptic, and the "Designs for Vision" Wide Angle Telescope. It is apparent that for any given magnification up to 2.5×, the combination of IOL plus spectacle lens yields a wider field of view than the conventional telescopic low vision aids.

Curve B in FIG. 4 illustrates the magnification and field obtainable with the combination of a contact lens and a spectacle lens. Since it is impractical to utilize contact lenses of extreme negative power, the curve is extended only to −30 D. Curve B indicates that the magnification obtainable with this combination is quite limited. Comparison with curve A shows that for a given magnification, the field obtainable with the IOL/spectacle combination is superior to that of the CL/spectacle combination.

FIG. 5 is a graphical representation of the relation between IOL power and magnification for various combinations of IOL and external lenses. Line A gives the magnification as a function of IOL power for the combination of an IOL and a spectacle lens located at a vertex distance of 13 mm (v = 0.013 m) from the cornea. This vertex distance is typical for many patients. Each figure in parenthesis is the required power of the external lens, the spectacle lens in this case. Line B is for the combination of an IOL together with a contact lens. It is apparent that this combination does not offer the degree of magnification that can be obtained with the IOL/spectacle combination. The reason is that the IOL and the CL are of necessity in fairly close proximity, as dictated by the anatomy of the eye.

Line C is for the more complex combination of an IOL, a contact lens of −20 D power, and a spectacle lens. This arrangement increases the magnification available compared to either of the above combinations. The price to be paid for this additional magnification is the inconvenience of wearing a contact lens as well as a spectacle lens, and the increased power necessary in the spectacle lens.

Line D represents the IOL/spectacle combination with a vertex distance of 23 mm for the spectacle. This additional 10 mm of vertex distance is seen to give a significant increase in magnification compared to line A. There are two implications to this observation. First, a given magnification can be for a spectacle lens diameter of 40 mm., and a 7 mm. distance between the cornea and nodal point of the eye, a spectacle lens power of 21.4 diopters will yield a field of view of about 26.84° using the above formula. Thus, fields of view of 27° or greater are possible achieved with a lower power IOL and lower power spectacle lens if the vertex distance can be somewhat greater than the standard 13 mm. Second, and perhaps more important, after an IOL has been in place for a few years, the patient may require increased magnification, due to progressive macular degeneration. Rather than risk a second operation to replace the IOL, the patient can be fitted with spectacles having a greater vertex distance. For example, if the IOL were a $-60$ D lens, the initial magnification for a vertex distance of 13 mm would be $1.97\times$. Later the magnification could be increased to $2.5\times$ by increasing the vertex distance to 23 mm, together with an appropriate change in the power of the spectacle lens. While an increase in vertex distance does create minor problems in fitting spectacle lenses and in cosmetic appearance, the disadvantages are less objectionable than the traditional telescopic spectacles or hand-held telescopes.

As seen from the information provided by the graphs, the system of the invention provides improved magnification and increased field of vision over systems which are commonly available, while being easier to use and being far more cosmetically acceptable. As was noted previously, it is a significant advantage of the invention that, for a given magnification, the intraocular lens-spectacle combination provides a larger field of view than any of the alternatives shown in FIG. 4.

Additional advantages of the inventive combination are lighter weight, and fewer optical elements to be maintained in alignment. Cosmetically, a simple lens in front of the eye, even a strong positive lens, is less objectionable than a telescope mounted on the spectacle frame, as is presently employed.

The advantages of a system providing a wide field of view are obvious. A wide field greatly increases the ability of the patient to move about, to avoid obstacles, and generally to function normally, and, therefore, provides a viable alternative to systems which have been proposed previously.

Figure 8:
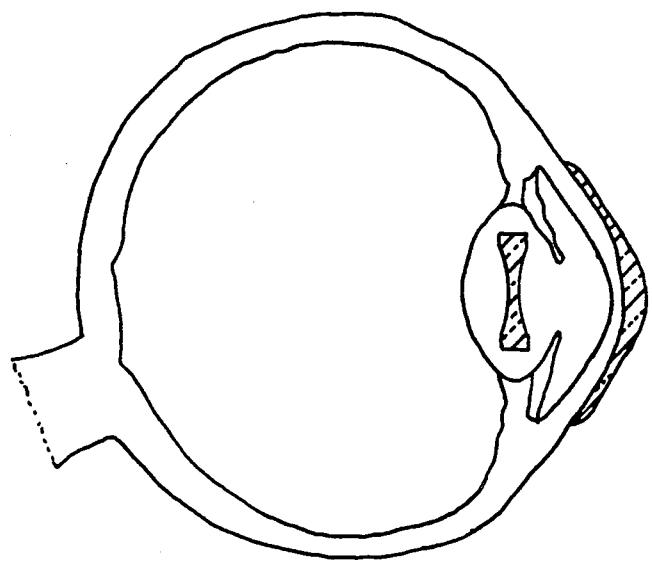
FIG. 8 illustrates a negative intraocular lens positioned in the posterior chamber in combination with a positive contact lens.

As has been noted above, the intraocular lens may be used in combination with a contact lens instead of a spectacle lens (FIG. 8). The negative intraocular lens and positive contact lens once again act to form a Galilean telescope. However, this embodiment is less preferred by virture of the shorter spacing between the two lenses, as compared with the spacing between the intraocular lens and a spectacle lens. The magnification which is obtained is, therefore, quite limited and fixed, as a result of the anatomy of the eye.

Figure 10:
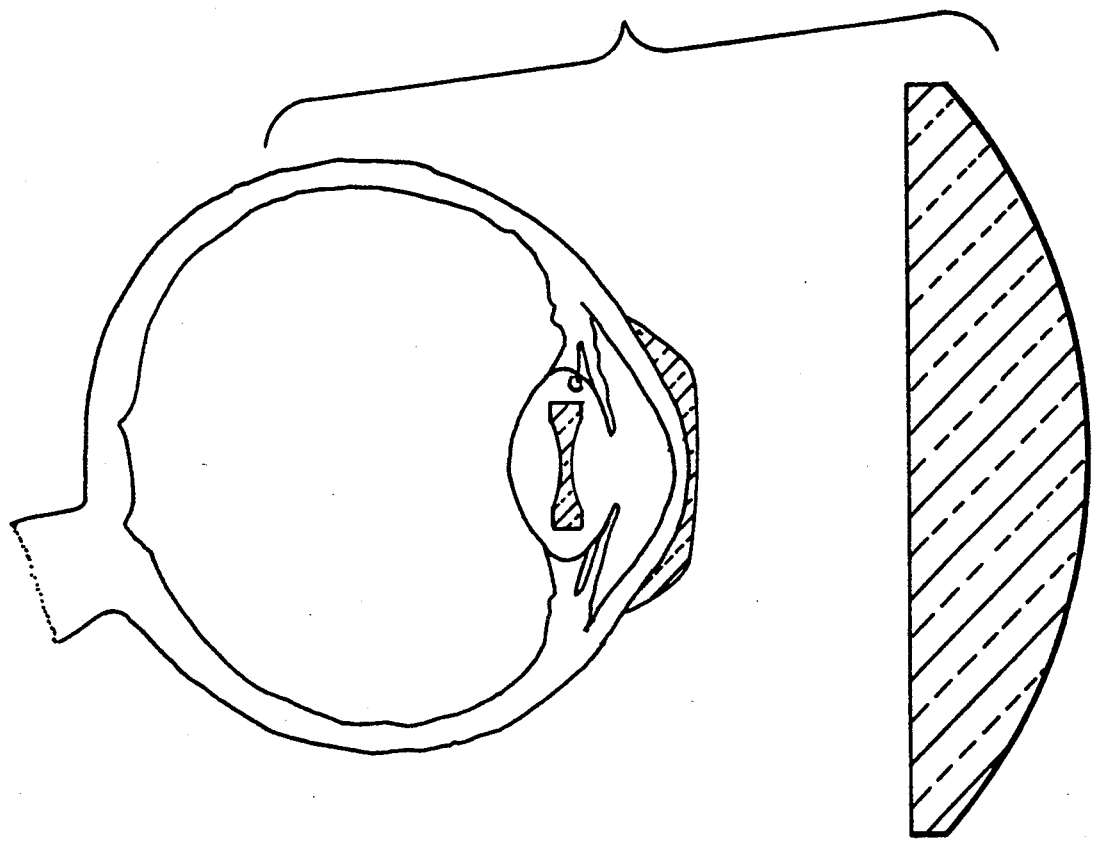
FIG. 10 illustrates a negative intraocular lens positioned in the posterior chamber in combination with a negative contact lens and a positive external spectacle lens.
Figure 11:
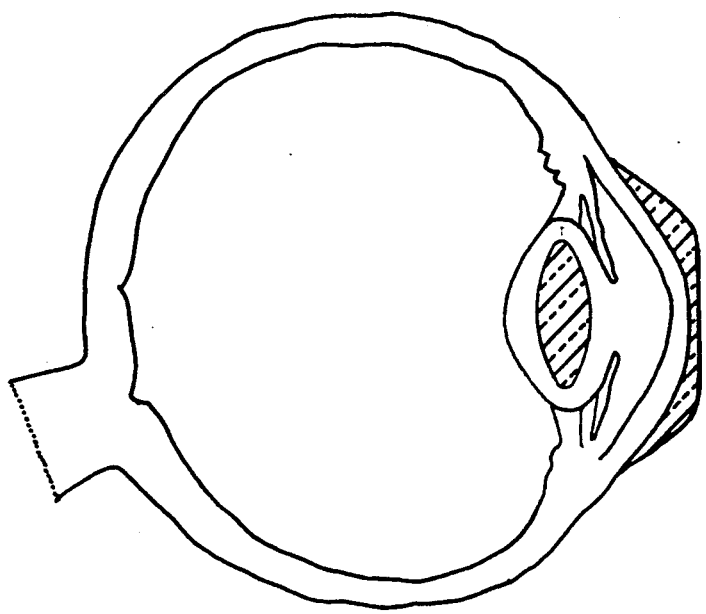
FIG. 11 illustrates a positive intraocular lens in the posterior chamber in combination with a negative contact lens.

In yet another embodiment of the invention (FIG. 10), a negative contact lens may be used in combination with a negative intraocular lens and a positive spectacle lens to satisfy the parameters set forth previously. However, by virtue of the extra problems associated with contact lens wear, as well as the additional problems of alignment of the three lenses, this system is likewise less preferable than the simple intraocular lens-spectacle lens system.

An additional embodiment of the invention employs a positive contact lens in combination with a positive spectacle lens and a negative intraocular lens. By dividing the required positive power between the spectacle lens and the contact lens, the power of the spectacle lens can be reduced, thus reducing its weight and improving the cosmetic appearance. Furthermore, for a given magnification, the field of view is somewhat greater for the combination including the positive contact lens than for the spectacle/IOL combination.

FIG. 7 illustrates an alternative embodiment of the invention which is useful with patients suffering from reduced peripheral vision. In this embodiment, the IOL and external lens powers are reversed such that the IOL 9' has a positive power while the external lens 7' has a negative power. A graph similar to that shown in FIG. 5 may be used for selecting various lens powers after the patient's visual requirements have been evaluated. By way of example, in this embodiment an IOL having a power of 40D in combination with a spectacle lens of $-25$D power at a vertex distance of 23 mm gives a magnification of 0.59.

Although the invention has been described with respect to particular materials, lenses, and intraocular lens systems, it is to be understood that the invention is not limited to the particulars disclosed, but extends to all equivalents falling within the scope of the claims.

We claim:

1. An intraocular lens sized and shaped for implantation in the posterior chamber of the eye, said lens comprising a negative-powered intraocular section having a power and being configured so as to provide substantial magnification of the retinal image and adapted to be used in combination with an external positive lens.

2. The intraocular lens as defined by claim 1, said lens having a power and being configured so as to provide a wide field of vision when used in combination with said external positive lens.

3. The intraocular lens as defined by claim 1 wherein said lens is provided with flexible support members adapted to position the lens in the posterior chamber of the eye.

4. The intraocular lens as defined by claim 1 wherein said lens has a negative power of at least $-10$ diopters.

5. The intraocular lens as defined by claim 4 wherein said lens has a negative power of at least $-40$ diopters.

6. An optical system comprising:
a) an intraocular lens comprising a negative-powered section sized and shaped for implantation within the posterior chamber of an eye; and
b) an external lens; whereby said intraocular lens and said external lens in combination have a power and are configured so as to provide substantial magnification of the retinal image.

7. The optical system as defined by claim 6 wherein said external lens is a spectacle lens having a positive power so as to magnify the image on the retina of the eye.

8. The optical system as defined by claim 6 wherein said external lens is a positive contact lens.

9. The optical system as defined by claim 6 wherein said external lens is a positive Fresnel lens.

10. The optical system as defined by claim 6 further comprising a second external lens, and wherein said first external lens is a positive spectacle lens, and said second external lens is a negative contact lens.

11. The optical system as defined by claim 6 where said external lens is a spectacle lens spaced from the cornea vertex by a vertex distance and wherein the power of the spectacle lens and said vertex distance are determined by the desired magnification.

12. A method for providing substantial magnification to a human eye, comprising the steps of:
 a) removing the natural lens;
 b) implanting an intraocular lens comprising a negative section within the posterior chamber of said eye; and
 c) providing an external positive lens whereby said intraocular lens and said positive external lens in combination interact to provide substantial magnification of the image on the retina of said eye.

13. The method as defined by claim 12 wherein said external lens is a positive contact lens.

14. The method as defined by claim 12 wherein said external positive lens is a Fresnel lens.

15. The method as defined by claim 12 wherein said external lens is a positive spectacle lens.

16. The method as defined by claim 12 further comprising providing a second external lens, and wherein said first external lens is a positive spectacle lens, and said second external lens is a negative contact lens.

17. The method as defined by claim 12 wherein said external lens is a positive spectacle lens and said method comprises adjusting the power and vertex distance of the spectacle lens from the cornea vertex in accordance with the desired magnification of the system.

18. An intraocular lens comprising a negative-powered section sized and shaped for implantation in the posterior chamber of the eye, said lens having a negative power greater than −40 diopters.

19. The intraocular lens as defined by claim 18 wherein said lens is provided with flexible support members.

20. An intraocular lens comprising a negative-powered section, said lens being sized and shaped for implantation in the eye, said lens providing greater than a 2× magnification power of the retinal image when used in combination with an external positive lens and a field of view of at least 27°.

21. The negative-powered intraocular lens as defined by claim 20, said intraocular lens being configured so as to provide a wide field of vision when used in combination with said external positive lens.

22. The negative-powered intraocular lens as defined by claim 20, wherein said intraocular lens is provided with flexible support members adapted to position said intraocular lens in the posterior chamber of the eye.

23. The negative-powered intraocular lens as defined by claim 20 wherein said intraocular lens has a negative power of at least −10 diopters.

24. The negative-powered intraocular lens as defined by claim 20 wherein said intraocular lens has a negative power of at least −40 diopters.

25. The negative-powered intraocular lens as defined by claim 20 wherein said intraocular lens is provided with flexible support members adapted to position said intraocular lens in the anterior chamber of the eye.

* * * * *